United States Patent
Moffitt et al.

(10) Patent No.: US 12,172,019 B2
(45) Date of Patent: *Dec. 24, 2024

(54) MACHINE LEARNING TO OPTIMIZE SPINAL CORD STIMULATION

(71) Applicant: Boston Scientific Neuromodulation Corporation, Valencia, CA (US)

(72) Inventors: Michael A. Moffitt, Solon, OH (US); Natalie A. Brill, Sherman Oaks, CA (US); Jianwen Gu, Richmond, TX (US); Juan Gabriel Hincapie Ordonez, Maple Grove, MN (US); Changfang Zhu, Valencia, CA (US); Hemant Bokil, Cambridge, MA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,623

(22) Filed: Apr. 26, 2023

(65) Prior Publication Data

US 2023/0256249 A1 Aug. 17, 2023

Related U.S. Application Data

(63) Continuation of application No. 17/027,453, filed on Sep. 21, 2020, now Pat. No. 11,666,761, which is a
(Continued)

(51) Int. Cl.
*A61N 1/36* (2006.01)
*A61N 1/02* (2006.01)
(Continued)

(52) U.S. Cl.
CPC ......... *A61N 1/36135* (2013.01); *A61N 1/025* (2013.01); *A61N 1/36007* (2013.01);
(Continued)

(58) Field of Classification Search
CPC ................ A61N 1/025; A61N 1/36003; A61N 1/36007; A61N 1/3605; A61N 1/36071;
(Continued)

(56) References Cited

U.S. PATENT DOCUMENTS 10,842,997 B2 * 11/2020 Moffitt ............... A61N 1/36071
11,666,761 B2 * 6/2023 Moffitt ............... A61N 1/36071
607/46
(Continued)

FOREIGN PATENT DOCUMENTS

CN 102238978 A 11/2011
CN 102413870 A 4/2012
(Continued)

OTHER PUBLICATIONS

"U.S. Appl. No. 15/244,913, Advisory Action mailed Oct. 26, 2018", 3 pgs.
(Continued)

*Primary Examiner* — Jon Eric C Morales
(74) *Attorney, Agent, or Firm* — Schwegman Lundberg & Woessner, P.A.

(57) ABSTRACT

An example of a system may include a processor and a memory device comprising instructions, which when executed by the processor, cause the processor to: access a patient metric of a subject; use the patient metric as an input to a machine learning algorithm, the machine learning algorithm to search a plurality of neuromodulation parameter sets and to identify a candidate neuromodulation parameter set of the plurality of neuromodulation parameter sets, the candidate neuromodulation parameter set designed to
(Continued)

produce a non-regular waveform that varies over a time domain and a space domain; and program a neuromodulator using the candidate neuromodulation parameter set to stimulate the subject.

20 Claims, 9 Drawing Sheets

Related U.S. Application Data continuation of application No. 15/244,913, filed on Aug. 23, 2016, now Pat. No. 10,842,997.

(60) Provisional application No. 62/277,686, filed on Jan. 12, 2016, provisional application No. 62/210,221, filed on Aug. 26, 2015.

(51) Int. Cl.
  *A61N 1/372* (2006.01)
  *G16H 50/20* (2018.01)
  *G16H 20/30* (2018.01)
  *G16H 50/70* (2018.01)
(52) U.S. Cl.
  CPC ....... *A61N 1/3605* (2013.01); *A61N 1/36071* (2013.01); *A61N 1/37247* (2013.01); *G16H 50/20* (2018.01); *A61N 1/36003* (2013.01); *A61N 1/36132* (2013.01); *A61N 1/36146* (2013.01); *G16H 20/30* (2018.01); *G16H 50/70* (2018.01)
(58) Field of Classification Search
  CPC ............ A61N 1/36132; A61N 1/36135; A61N 1/36146; A61N 1/37247; G16H 20/30; G16H 50/20; G16H 50/70
  See application file for complete search history.

(56) References Cited

U.S. PATENT DOCUMENTS

| | | | |
|---|---|---|---|
| 2009/0281594 | A1 | 11/2009 | King et al. |
| 2012/0016435 | A1 | 1/2012 | Rom |
| 2014/0074179 | A1 | 3/2014 | Heldman et al. |
| 2014/0163640 | A1 | 6/2014 | Edgerton et al. |
| 2014/0277267 | A1 | 9/2014 | Vansickle et al. |
| 2014/0350634 | A1 | 11/2014 | Grill et al. |
| 2015/0005680 | A1 | 1/2015 | Lipani |
| 2015/0132396 | A1 | 5/2015 | Coulter et al. |
| 2015/0231396 | A1 | 8/2015 | Burdick et al. |
| 2017/0056642 | A1 | 3/2017 | Moffitt et al. |
| 2017/0095667 | A1 | 4/2017 | Yakovlev et al. |
| 2021/0069512 | A1 | 3/2021 | Moffitt et al. |

FOREIGN PATENT DOCUMENTS

| | | |
|---|---|---|
| CN | 103608069 A | 2/2014 |
| CN | 107921262 A | 4/2018 |
| CN | 107921262 B | 6/2021 |
| EP | 3341073 B1 | 7/2023 |
| WO | WO-2014113813 A1 | 7/2014 |
| WO | WO-2017035140 A1 | 3/2017 |

OTHER PUBLICATIONS

"U.S. Appl. No. 15/244,913, Advisory Action mailed Nov. 3, 2017", 3 pgs.
"U.S. Appl. No. 15/244,913, Examiner Interview Summary mailed Jan. 15, 2020", 3 pgs.
"U.S. Appl. No. 15/244,913, Examiner Interview Summary mailed Jun. 16, 2020", 3 pgs.
"U.S. Appl. No. 15/244,913, Examiner Interview Summary mailed Oct. 12, 2018", 3 pgs.
"U.S. Appl. No. 15/244,913, Final Office Action mailed Apr. 6, 2020", 17 pgs.
"U.S. Appl. No. 15/244,913, Final Office Action mailed May 3, 2019", 15 pgs.
"U.S. Appl. No. 15/244,913, Final Office Action mailed Aug. 1, 2018", 13 pgs.
"U.S. Appl. No. 15/244,913, Final Office Action mailed Sep. 5, 2017", 10 pgs.
"U.S. Appl. No. 15/244,913, Non Final Office Action mailed Jan. 17, 2018", 11 pgs.
"U.S. Appl. No. 15/244,913, Non Final Office Action mailed Mar. 24, 2017", 9 pgs.
"U.S. Appl. No. 15/244,913, Non Final Office Action mailed Sep. 25, 2019", 15 pgs.
"U.S. Appl. No. 15/244,913, Non Final Office Action mailed Nov. 15, 2018", 14 pgs.
"U.S. Appl. No. 15/244,913, Notice of Allowance mailed Jul. 22, 2020", 8 pgs.
"U.S. Appl. No. 15/244,913, Response filed Jan. 20, 2020 to Non Final Office Action mailed Sep. 25, 2019", 7 pgs.
"U.S. Appl. No. 15/244,913, Response filed Feb. 13, 2019 to Non Final Office Action mailed Nov. 15, 2018", 10 pgs.
"U.S. Appl. No. 15/244,913, Response filed Apr. 12, 2018 to Non Final Office Action mailed Jan. 17, 2017", 8 pgs.
"U.S. Appl. No. 15/244,913, Response filed Jun. 11, 2020 to Final Office Action mailed Apr. 6, 2020", 10 pgs.
"U.S. Appl. No. 15/244,913, Response filed Jun. 21, 2017 to Non Final Office Action mailed Mar. 24, 2017", 6 pgs.
"U.S. Appl. No. 15/244,913, Response filed Sep. 3, 2019 to Final Office Action mailed May 3, 2019", 11 pgs.
"U.S. Appl. No. 15/244,913, Response filed 10-115-18 to Final Office Action mailed Aug. 1, 2018", 8 pgs.
"U.S. Appl. No. 15/244,913, Response filed Oct. 24, 2017 to Final Office Action mailed Sep. 5, 2017", 9.
"U.S. Appl. No. 15/244,913, Response filed Dec. 4, 2017 to Final Office Action mailed Sep. 5, 2017", 13 pgs.
"U.S. Appl. No. 17/027,453, Non Final Office Action mailed Oct. 12, 2022", 6 pgs.
"U.S. Appl. No. 17/027,453, Notice of Allowance mailed Jan. 31, 2023", 7 pgs.
"U.S. Appl. No. 17/027,453, Response filed Jan. 5, 2023 to Non Final Office Action mailed Oct. 12, 2022", 6 pgs.
"Chinese Application Serial No. 201680049020.5, Office Action mailed Jul. 24, 2020", with English translation, 14 pgs.
"Chinese Application Serial No. 201680049020.5, Office Action mailed Dec. 28, 2020", with English translation, 14 pgs.
"Chinese Application Serial No. 201680049020.5, Response filed Mar. 12, 2021 to Office Action mailed Dec. 28, 2020", w/ English Claims, 9 pgs.
"Chinese Application Serial No. 201680049020.5, Response filed Dec. 7, 2020 to Office Action mailed Jul. 24, 2020", w/ English claims, 10 pgs.
"European Application Serial No. 16757528.1, Communication Pursuant to Article 94(3) EPC mailed May 24, 2022", 4 pgs.
"European Application Serial No. 16757528.1, Response filed Sep. 14, 2022 to Communication Pursuant to Article 94(3) EPC mailed May 24, 2022", Claims not amended in response filed, 17 pgs.
"European Application Serial No. 16757528.1, Response filed Nov. 15, 2018 to Communication Pursuant to Rules 161 and 162 EPC mailed May 7, 2018", 15 pgs.
"International Application Serial No. PCT/US2016/048195, International Preliminary Report on Patentability mailed Mar. 8, 2018", 9 pgs.
"International Application Serial No. PCT/US2016/048195, International Search Report mailed Nov. 29, 2016", 9 pgs.
"International Application Serial No. PCT/US2016/048195, Written Opinion mailed Nov. 29, 2016", 8 pgs.
Alo, Kenneth, et al., "Effect of Spinal Cord Stimulation on Sensory Nerve Conduction Threshold Functional Measures", Neuromodulation. Aug. 2000;3(3): 145-54, (Aug. 2000), 145-154.

(56) References Cited

OTHER PUBLICATIONS

Dansie, Elizabeth, et al., "Association of Chronic Widespread Pain With Objectively Measured Physical Activity in Adults: Findings From the National Health and Nutrition Examination Survey", The Journal of Pain, vol. 15, No. 5, (May 2014), 507-515.

Eisenberg, Elon, et al., "Quantitative Sensory Testing for Spinal Cord Stimulation in Patients With Chronic Neuropathic Pain", Pain Practice, vol. 6, Issue 3, (2006), 161-165.

Granovsky, Yelena, et al., "Objective Correlate of Subjective Pain Perception by Contact Heat-Evoked Potentials", The Journal of Pain, vol. 9, No. 1, (Jan. 2008), 53-63.

Kemler, Marius, et al., "Impact of Spinal Cord Stimulation on Sensory Characteristics in Complex Regional Pain Syndrome Type I—A Randomized Trial", Anesthesiology 2001; 95:72-80, (2001), 72-80.

Leblanc, Brian, et al., "Cortical theta is increased while thalamocortical coherence is decreased in rat models of acute and chronic pain", PAIN 155, (2014), 773-782.

Maier, C., et al., "Quantitative sensory testing in the German Research Network on Neuropathic Pain (DFNS): Somatosensory abnormalities in 1236 patients with different neuropathic pain syndromes", Pain 150, (2010), 439-450.

Marchand, S., et al., "The effects of dorsal column stimulation on measures of clinical and experimental pain in man", Pain, 45, (1991), 249-257.

Mironer, Y., et al., "Pain Tolerance Threshold: A Pilot Study of an Objective Measurement of Spinal Cord Stimulator Trial Results", Pain Medicine; vol. 1, No. 2, (2000), 110-115.

Moseley, G., et al., "Tactile discrimination, but not tactile stimulation alone, reduces chronic limb pain", Pain 137, (2008), 600-608.

Peng, Weiwei, et al., "Changes of Spontaneous Oscillatory Activity to Tonic Heat Pain", PLoS ONE 9(3), e91052, (Mar. 2014), 1-11.

Pleger, Burkhard, et al., "Patterns of cortical reorganization parallel impaired tactile discrimination and pain intensity in complex regional pain syndrome", NeuroImage 32, (2006), 503-510.

Pluijms, Wouter, et al., "Increased Contact Heat Evoked Potential Stimulation Latencies in Responders to Spinal Cord Stimulation for Painful Diabetic Polyneuropathy", Neuromodulation 2015; 18, (Mar. 24, 2014), 126-132.

Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.

Saab, Carl, "Pain-related changes in the brain: diagnostic and therapeutic potentials", Trends in Neurosciences; vol. 35, No. 10, (Oct. 2012), 629-637.

Sarnthein, J., et al., "Increased EEG power and slowed dominant frequency in patients with neurogenic pain", Brain (2006), 129, (2006), 55-64.

Sato, Karina, et al., "Spinal Cord Stimulation (SCS) Improves Decreased Physical Activity Induced by Nerve Injury", Behavioral Neuroscience @ 2014 American Psychological Association, 2014, vol. 128, No. 5, (2014), 625-632.

Schulz, Enrico, et al., "Prefrontal Gamma Oscillations Encode Tonic Pain in Humans", Cerebral Cortex, 2015, 1-8, (Mar. 8, 2015), 1-8.

Staud, Roland, "Heart rate variability as a biomarker of fibromyalgia syndrome", Fut Rheumatol. Oct. 1, 2008; 3(5), (Oct. 1, 2008), 475-483.

Theuvenet, P., et al., "Responses to Median and Tibial Nerve Stimulation in Patients with Chronic Neuropathic Pain", Brain Topography, vol. 11, No. 4, (1999), 305-313.

\* cited by examiner

MACHINE LEARNING TO OPTIMIZE SPINAL CORD STIMULATION

CLAIM OF PRIORITY

This application is a continuation of U.S. application Ser. No. 17/027,453, filed Sep. 21, 2020, now issued as U.S. Pat. No. 11,666,761, which is a continuation of U.S. application Ser. No. 15/244,913, filed Aug. 23, 2016, now issued as U.S. Pat. No. 10,842,997, which claims the benefit of priority under 35 U.S.C. § 119(e) of U.S. Provisional Patent Application Ser. No. 62/210,221, filed on Aug. 26, 2015, and U.S. Provisional Patent Application Ser. No. 62/277,686, filed on Jan. 12, 2016, all of which are herein incorporated by reference in its entireties.

TECHNICAL FIELD

This document relates generally to medical devices, and more particularly, to systems, devices, and methods for delivering neural modulation.

BACKGROUND

Neuromodulation, which includes neurostimulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

The neurostimulation energy may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body.

SUMMARY

Example 1 includes subject matter (such as a method, means for performing acts, machine readable medium including instructions that when performed by a machine cause the machine to performs acts, or an apparatus to perform) comprising: accessing, at a computerized system, a patient metric of a subject; using the patient metric as an input to a machine learning algorithm executing on the computerized system, the machine learning algorithm to search a plurality of neuromodulation parameter sets and to identify a candidate neuromodulation parameter set of the plurality of neuromodulation parameter sets, the candidate neuromodulation parameter set designed to produce a non-regular waveform that varies over a time domain and a space domain; and programming a neuromodulator using the candidate neuromodulation parameter set to stimulate the subject.

In Example 2, the subject matter of Example 1 may include, wherein the subject is a patient.

In Example 3, the subject matter of any one of Examples 1 to 2 may include, wherein the subject is an animal from a preclinical trial.

In Example 4, the subject matter of any one of Examples 1 to 3 may include, wherein the machine learning algorithm comprises a genetic algorithm.

In Example 5, the subject matter of any one of Examples 1 to 4 may include, wherein the machine learning algorithm comprises a neural network.

In Example 6, the subject matter of any one of Examples 1 to 5 may include, wherein the computerized system is a cloud-based system, and wherein programming the neuromodulator comprises transmitting the candidate neuromodulation parameter set to a client device of the cloud-based system.

In Example 7, the subject matter of any one of Examples 1 to 6 may include, wherein the patient metric is an objective pain metric.

In Example 8, the subject matter of any one of Examples 1 to 7 may include, wherein the objective pain metric is a physiological indication sensed by a sensor worn by the subject.

In Example 9, the subject matter of any one of Examples 1 to 8 may include, wherein the patient metric is a subjective pain metric.

In Example 10, the subject matter of any one of Examples 1 to 9 may include, wherein the subjective pain metric is obtained from querying the subject.

In Example 11, the subject matter of any one of Examples 1 to 10 may include, wherein the space domain includes at least one parameter related to fractionalization or polarity.

In Example 12, the subject matter of any one of Examples 1 to 11 may include, wherein the candidate neuromodulation parameter set is designed to produce a pulse burst that varies pulse-by-pulse.

In Example 13, the subject matter of any one of Examples 1 to 12 may include, receiving from a user, a selected parameter; and focusing the machine learning algorithm using the selected parameter.

Example 14 includes a machine-readable medium including instructions, which when executed by a machine, cause the machine to perform operations of any of the Examples 1-13.

Example 15 includes an apparatus comprising means for performing any of the Examples 1-13.

Example 16 includes subject matter (such as a device, apparatus, or machine) comprising: a processor; and a memory device comprising instructions, which when executed by the processor, cause the processor to: access a patient metric of a subject; use the patient metric as an input to a machine learning algorithm, the machine learning algorithm to search a plurality of neuromodulation parameter sets and identify a candidate neuromodulation parameter set of the plurality of neuromodulation parameter sets, the candidate neuromodulation parameter set designed to produce a non-regular waveform that varies over a time domain and a space domain; and program a neuromodulator using the candidate neuromodulation parameter set to stimulate the subject.

In Example 17, the subject matter of Example 16 may include, wherein the subject is a patient.

In Example 18, the subject matter of any one of Examples 16 to 17 may include, wherein the subject is an animal from a preclinical trial.

In Example 19, the subject matter of any one of Examples 16 to 18 may include, wherein the machine learning algorithm comprises a genetic algorithm.

In Example 20, the subject matter of any one of Examples 16 to 19 may include, wherein the machine learning algorithm comprises a neural network.

In Example 21, the subject matter of any one of Examples 16 to 20 may include, wherein the system is a cloud-based system, and wherein the instructions to provide the candidate neuromodulation parameter set comprise instructions to transmit the candidate neuromodulation parameter set to a client device of the cloud-based system.

In Example 22, the subject matter of any one of Examples 16 to 21 may include, wherein the patient metric is an objective pain metric.

In Example 23, the subject matter of any one of Examples 16 to 22 may include, wherein the objective pain metric is a physiological indication sensed by a sensor worn by the subject.

In Example 24, the subject matter of any one of Examples 16 to 23 may include, wherein the patient metric is a subjective pain metric.

In Example 25, the subject matter of any one of Examples 16 to 24 may include, wherein the subjective pain metric is obtained from querying the subject.

In Example 26, the subject matter of any one of Examples 16 to 25 may include, wherein the space domain includes at least one parameter related to fractionalization or polarity.

In Example 27, the subject matter of any one of Examples 16 to 26 may include, wherein the candidate neuromodulation parameter set is designed to produce a pulse burst that varies pulse-by-pulse.

In Example 28, the subject matter of any one of Examples 16 to 27 may include, wherein the memory device further comprises instructions, which when executed by the processor, cause the processor to: receive from a user, a selected parameter; and focus the machine learning algorithm using the selected parameter.

Example 29 includes subject matter (such as a method, means for performing acts, machine readable medium including instructions that when performed by a machine cause the machine to performs acts, or an apparatus to perform) comprising: accessing, at a computerized system, a patient metric of a subject; using the patient metric as an input to a machine learning algorithm executing on the computerized system, the machine learning algorithm to search a plurality of neuromodulation parameter sets and to identify a candidate neuromodulation parameter set of the plurality of neuromodulation parameter sets, the candidate neuromodulation parameter set designed to produce a non-regular waveform that varies over a time domain and a space domain; programming a neuromodulator using the candidate neuromodulation parameter set to stimulate the subject; and producing the non-regular waveform.

In Example 30, the subject matter of Example 29 may include, wherein the subject is a patient.

In Example 31, the subject matter of any one of Examples 29 to 30 may include, wherein the subject is an animal from a preclinical trial.

In Example 32, the subject matter of any one of Examples 29 to 31 may include, wherein the machine learning algorithm comprises a genetic algorithm.

In Example 33, the subject matter of any one of Examples 29 to 32 may include, wherein the candidate neuromodulation parameter set is designed to produce a pulse burst that varies pulse-by-pulse.

In Example 34, the subject matter of any one of Examples 29 to 33 may include, receiving from a user, a selected parameter; and focusing the machine learning algorithm using the selected parameter.

Example 35 includes subject matter (such as a machine-readable medium, computer-readable medium, or other stored instructions) comprising instructions, which when executed, cause a device to: access a patient metric of a subject; use the patient metric as an input to a machine learning algorithm, the machine learning algorithm to search a plurality of neuromodulation parameter sets and to identify a candidate neuromodulation parameter set of the plurality of neuromodulation parameter sets, the candidate neuromodulation parameter set designed to produce a non-regular waveform that varies over a time domain and a space domain; and program a neuromodulator using the candidate neuromodulation parameter set to stimulate the subject.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
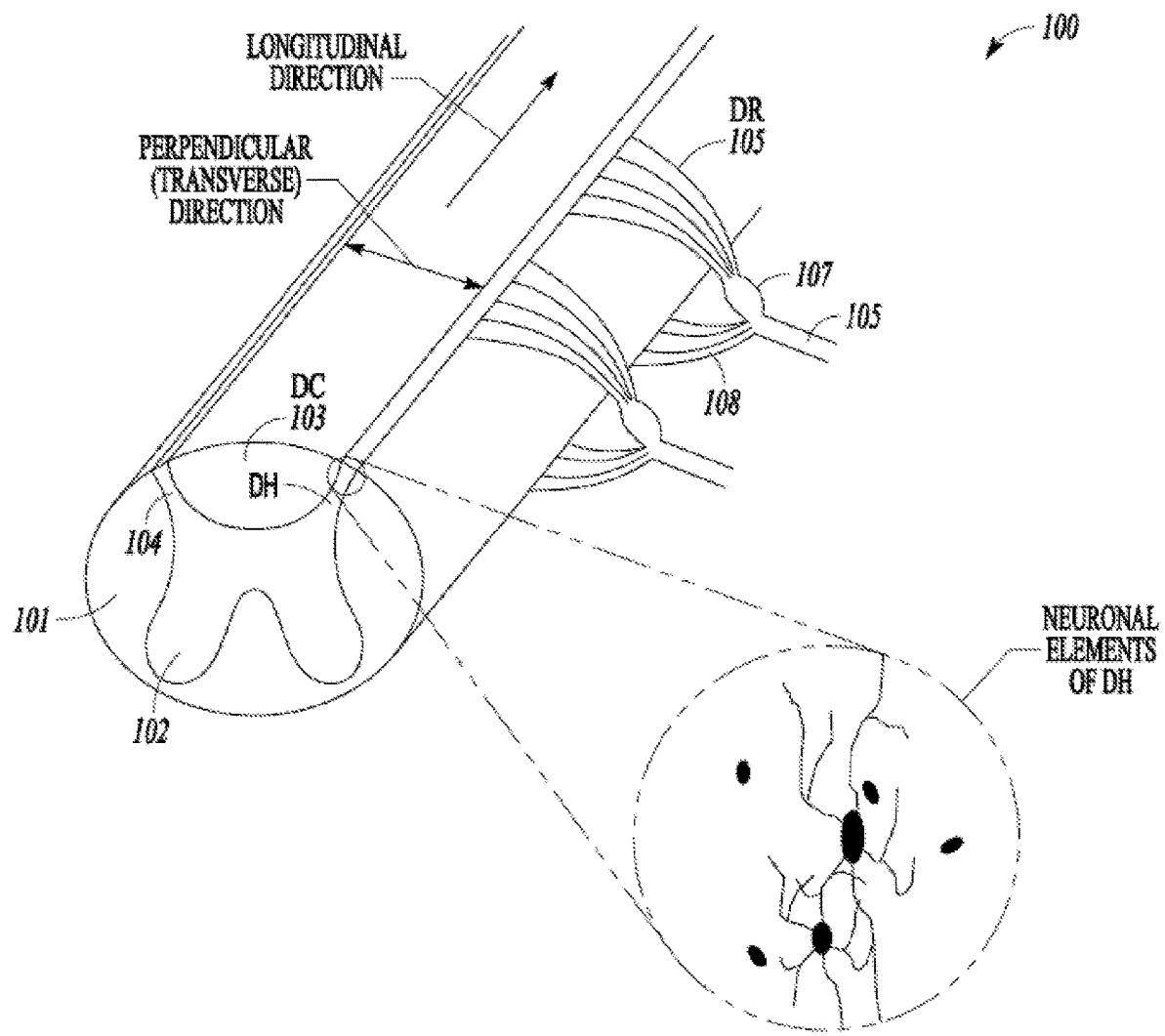
FIG. 1 illustrates a portion of a spinal cord.

Various embodiments described herein involve spinal cord modulation. A brief description of the physiology of the spinal cord and related apparatus is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Some embodiments deliver therapy where the delivery of energy is perceptible due to sensations such as paresthesia. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
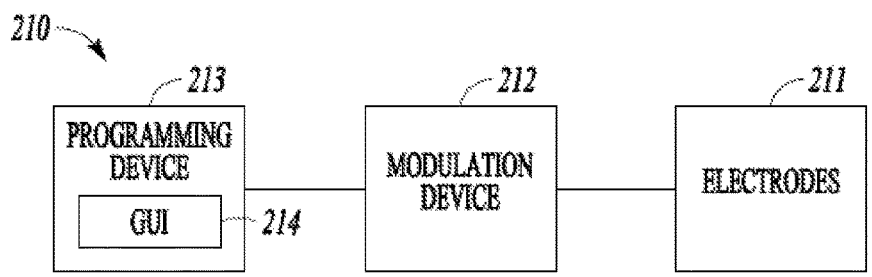
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
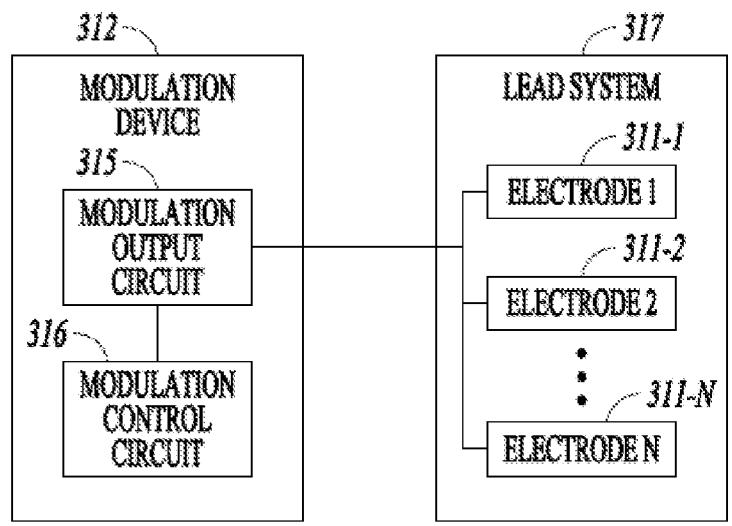
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of available modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets. A closed-loop mechanism may be used to identify and test modulation parameter sets, receive patient or clinician feedback, and further revise the modulation parameter sets to attempt to optimize stimulation paradigms for pain relief. The patient or clinician feedback may be objective and/or subjective metrics reflecting pain, paresthesia coverage, or other aspects of patient satisfaction with the stimulation.

Figure 4:
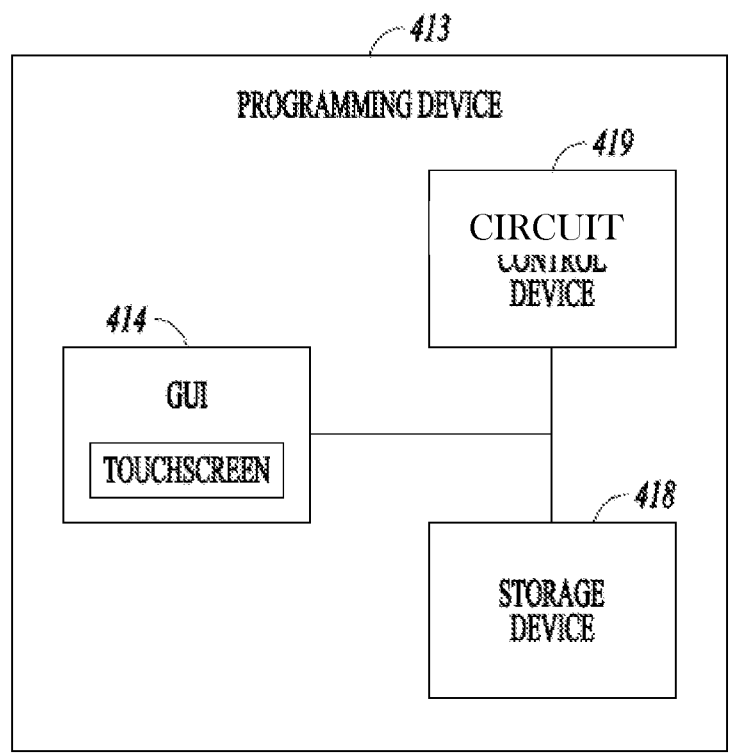
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device (e.g., modulation device 312 of FIG. 3). The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software, and firmware. For example, the circuit of GUI 414, modulation control circuit 316, and programming control circuit 419, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or a portion thereof, and a programmable logic circuit or a portion thereof.

Figure 5:
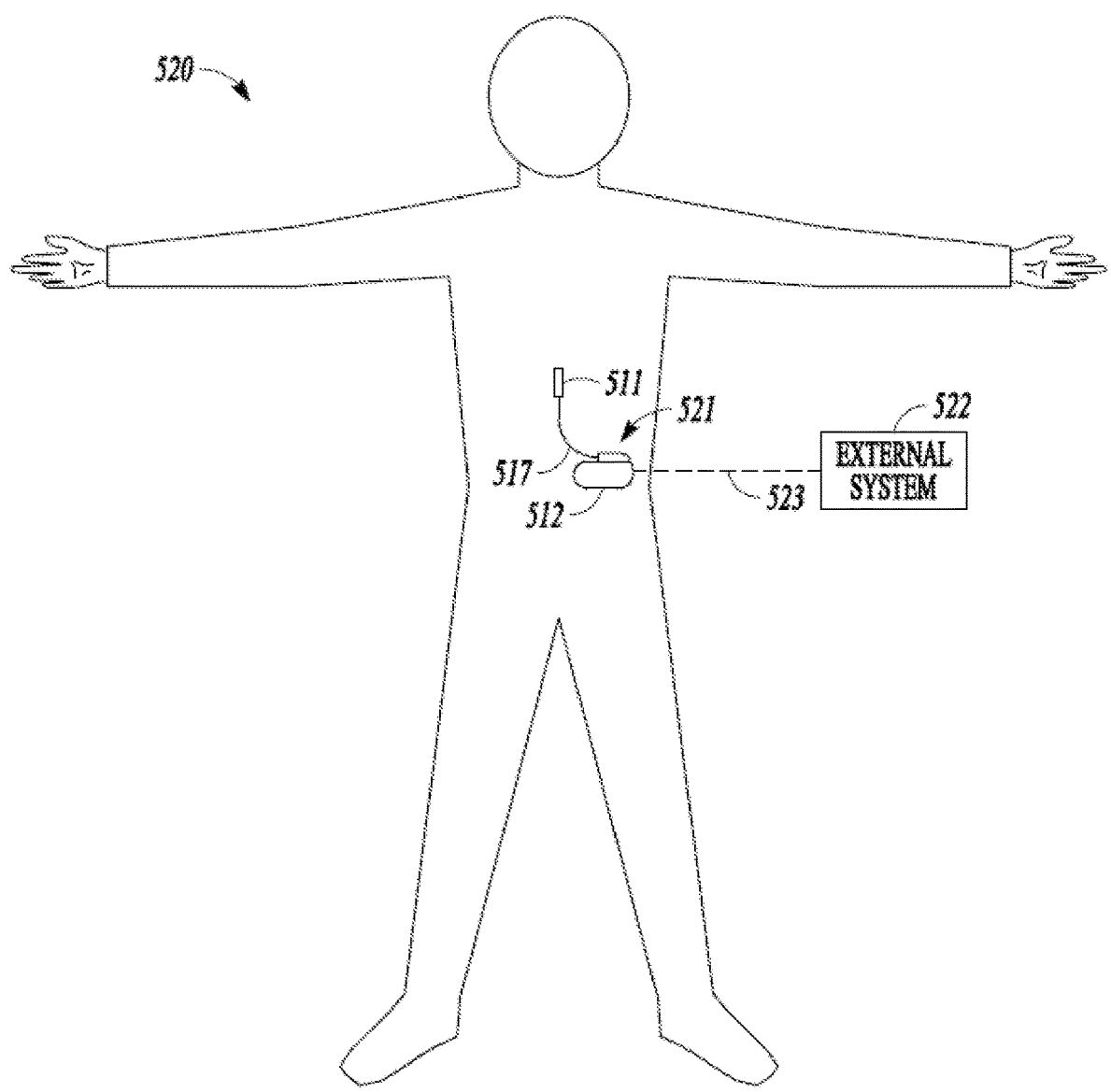
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system 521 is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters. The remote control device may also provide a mechanism for the patient to provide feedback on the operation of the implantable neuromodulation system. Feedback may be metrics reflecting perceived pain, effectiveness of therapies, or other aspects of patient comfort or condition.

The neuromodulation lead(s) of the lead system 517 may be placed adjacent, e.g., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Application of Machine Learning to Optimize Stimulation Parameters

Identifying optimized stimulation patterns to relive pain in neuromodulation (e.g., SCS) is challenging because the parameter space is so large, objective metrics to assess patient pain are not used, and response latency may be long (e.g., up to days). A machine learning system may be used in a closed-loop hybrid clinical or pre-clinical process to develop optimized stimulation patterns for pain management. The stimulation patterns may be modulated in both the time and space domains.

An initial set of stimulation patterns may be generated from a domain of all available stimulation patterns. The initial set may be based on preclinical pain trials. The initial set may be obtained using one or more machine learning or optimization algorithms to search for and identify effective patterns.

In the clinical system, a patient may be provided one or more stimulation patterns, which may be tested by the patient with or without clinician supervision. Objective pain metrics, subjective pain metrics, or both objective and subjective pain metrics may be received from the patient, which are used in the machine learning or optimization algorithms to develop further sets of patterns. Objective pain metrics include those that are physiologically expressed, such as EEG activity, heart rate, heart rate variability, galvanic skin response, or the like. Subjective pain metrics may be provided by the patient and be expressed as "strong pain," "lower pain," or numerically in a range, for example. The pain metrics may be communicated using various communication mechanisms, such as wireless networks, tethered communication, short-range telemetry, or combinations of such mechanisms. The patient may manually input some information (e.g., subjective pain scores).

A non-exhaustive list of pain metrics is provided herein. One example of a pain metric is EEG activity (e.g., Theta activity in the somatosensory cortex and alpha and gamma activity in the prefrontal cortex have been shown to correlate with pain). Another example pain metric is fMRI (activity in the anterior cingulate cortex and insula have been shown to correlate with changes in chronic pain). Another example pain metric is fMRI (activity in the pain matrix, which consists of the thalamus, primary somatosensory cortex, anterior cingulate cortex, prefrontal cortex, and cerebellum and is activated in pain conditions). Another example pain metric is heart rate variability, galvanic skin response, cortisol level, and other measures of autonomic system functioning (autonomic system health has been shown to correlate with pain). Another example pain metric is physical activity (amount of physical activity has been shown to correlate with pain). Another example pain metric is pain scores (may be inputted through an interface where the patient selects a point on a visual analog scale, or clicks a number on a numerical rating scale). Another example pain metric is quantitative sensory testing [e.g., spatial discrimination (two-point, location, diameter), temporal discrimination, detection threshold (mechanical, thermal, electrical), pain threshold (mechanical, thermal, electrical), temporal summation, thermal grill] (QST measures have been shown to correlate with pain). Another example pain metric is somatosensory evoked potentials, contact heat evoked potentials (these have been shown to be correlated with pain). Another example pain metric is H-reflex, nociceptive flexion reflex (these have been shown to be reduced by SCS). Another example pain metric is conditioned place preference (e.g., in one chamber, stimulate with one paradigm 1, in other chamber, stimulate with paradigm 2. The chamber where the animal spends the most time wins and continues to the next round). Another example pain metric is local field potential recordings in the pain matrix (recordings of neural activity in these areas are possible with invasive electrodes in a preclinical model).

Some pain metrics are primarily preclinical in nature (e.g., conditioned place preference and local field potential recordings), while others are primarily clinical in nature (e.g., pain scores and quantitative sensory testing). However, it is understood that the pain metrics may be obtained in either preclinical or clinical settings.

Pain metrics may be continuously or repeatedly collected from patients and fed into the machine learning or optimization algorithms to refine or alter the stimulation patterns.

For example, the patients may interact with a programmer, remote control, bedside monitor, or other patient device to record physical condition, pain, medication dosages, etc. The patient device may be wired or wirelessly connected to the system with the machine learning system. This closed-loop mechanism provides an advantage of reducing the search domain during repeated iterations of the machine learning or optimization algorithm. By reducing the search domain, a clinician is able to more quickly identify efficacious patterns and a patient may be subjected to shorter programming sessions, which produce less discomfort.

The physical system may take on many different forms. Data collected from the patient or pre-clinical model may be measured using wearable sensors (e.g., heart rate monitor, accelerometer, EEG headset). The pain metrics requiring manual input may be entered via remote control or other external device used by the patient (e.g. cellular phone).

Figure 6:
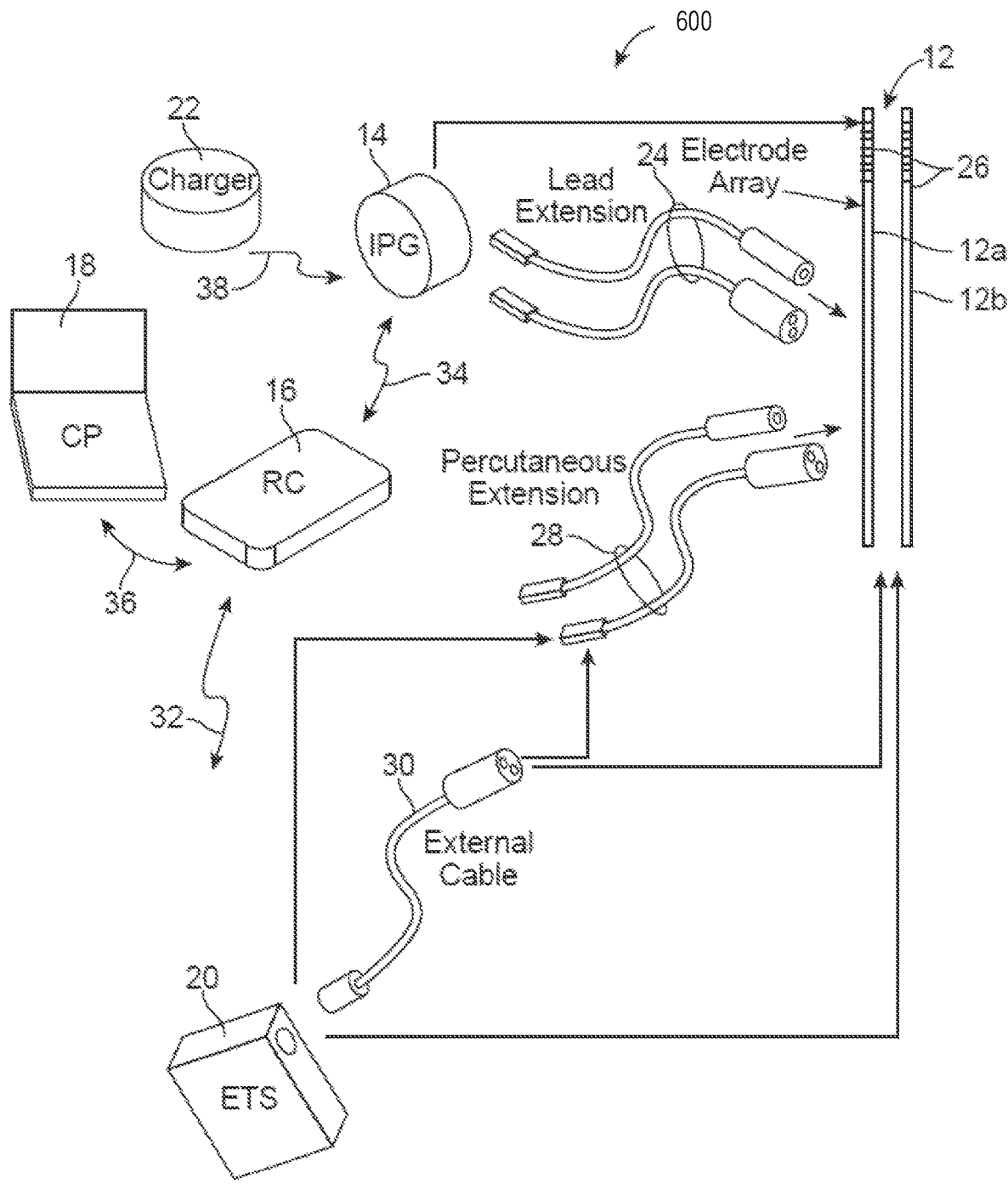
FIG. 6 illustrates, by way of example, an embodiment of an SCS system.

FIG. 6 illustrates, by way of example, an embodiment of an SCS system 600. The SCS system 600 generally comprises a plurality of neurostimulation leads 12 (in this case, two percutaneous leads 12a and 12b), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides the user detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the RC 16, ETS 20, and external charger 22 will not be described herein.

The algorithm may reside on the CP, the IPG, the ETS, the RC or other external device used by the patient, or in the cloud or remote servers connected to patient external via Wi-Fi, Bluetooth, cellular data, or other wired/wireless scheme. There may be a GUI on the CP, remote control, or other external device, that enables selection of algorithm as well as manual input. Training of the algorithm may take place in the clinic or in daily life, and may be set to be execute continually or only at certain times. Optimization data may be stored in the cloud so that optimized patterns and history can be transferred when the patient moves from trial to permanent implant and also if the IPG is replaced.

Figure 7:
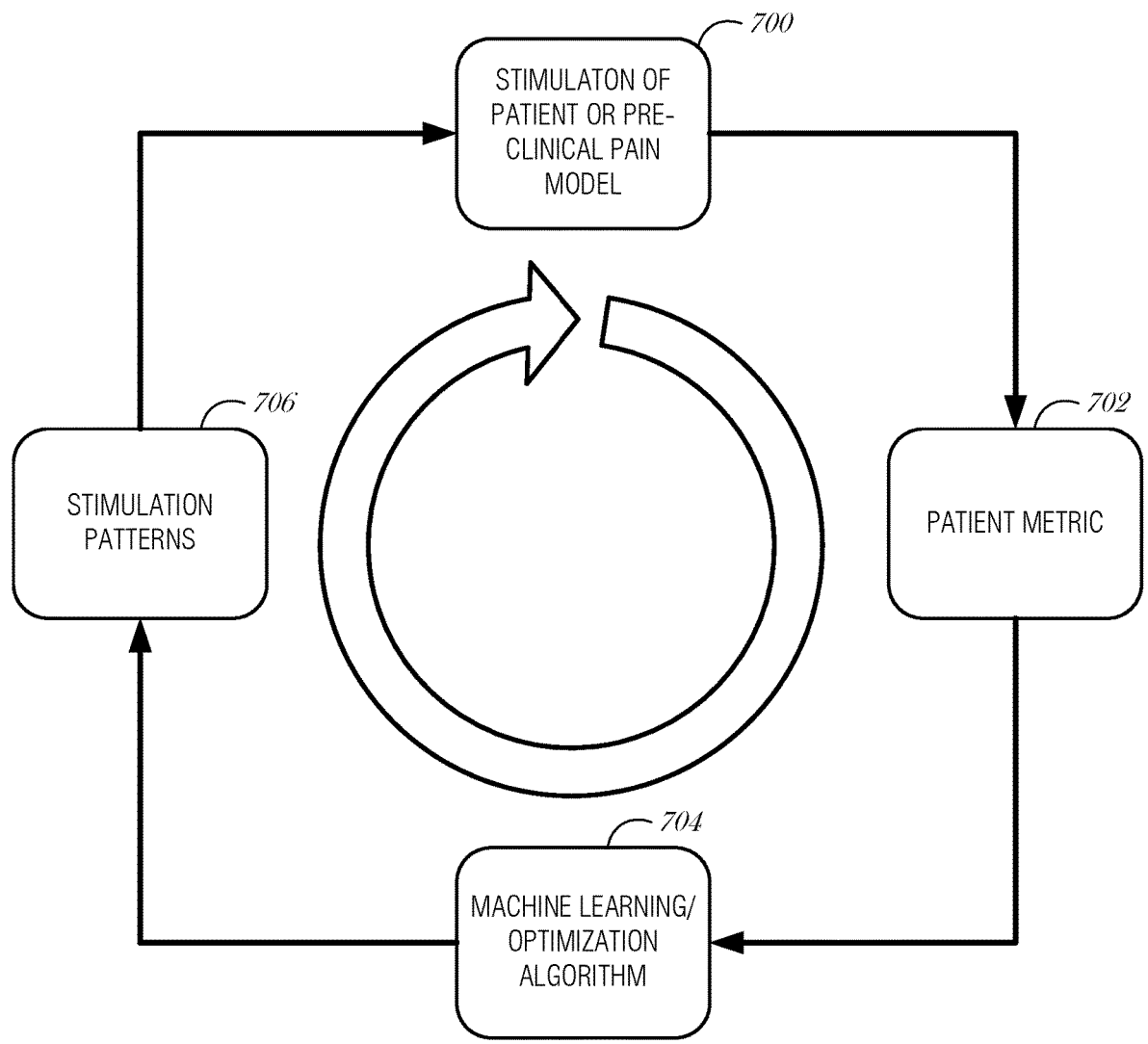
FIG. 7 illustrates, by way of example, an embodiment of data and control flow in a system that utilizes machine learning to optimize neurostimulation patterns.

FIG. 7 illustrates, by way of example, an embodiment of data and control flow in a system that utilizes machine learning to optimize neurostimulation patterns. A preclinical pain model may be used or alternatively, the feedback from a previous stimulation may be used to initialize the system (block 700). The patient is stimulated and one or more patient metrics are obtained (block 702). The patient metrics may be obtained via passive or active participation with the patient. For example, the patient metrics may be derived from sensing and correlating physiological changes or states in the patient. In this case, the patient provides the patient metrics passively-without active participation. Alternatively, the patient may be prompted (e.g., by a clinician or with an electronic graphical user interface) to provide a patient metric. Patient metrics gathered during passive participation may be referred to as objective pain measurements because they are typically physiological responses that are mostly uncontrollable by the patient, such as EEG activity or heart rate variability. Some patient metrics gathered via active participation with the patient may be referred to as subjective patient metrics, where the patient is asked to describe the pain. The patient metrics may include various aspects of pain, such as the severity as measured with a numerical value, the location(s) of pain, the sensation of pain (e.g., numbness, shape acute pain, throbbing, etc.), the duration of pain, or other aspects of pain. The patient metrics may also include results of questionnaires, responses to queries about a general state of wellness, results of memory tests (e.g., working memory tasks), rating scales, and the like.

The patient metric(s) are used as input to the machine learning or optimization algorithm (block 704). Various algorithms may be used, such as genetic algorithms, neural networks, or reinforcement learning strategies (e.g., Q-learning, Temporal Difference learning, or Markov decision processes). The machine learning or optimization algorithm may modify one or more variables, such as time delays, amplitudes of one or more pulses in a stimulation train, pulse shape, fractionalization, or pulse-by-pulse changes in spatial location of stimulation.

In a preclinical setting, objective patient metrics may be gathered from a study (e.g., an animal study) and used to identify a subset of parameter settings that may be used as an initial setting in a clinical environment. One benefit of the preclinical-machine learning closed-loop system is that much more time can be spent on optimization. Another benefit is that more invasive measures of pain can be used (e.g. electrodes implanted in the brain). As such, some embodiments use the preclinical system first to identify stimulation paradigms that are better than others, and then use the clinical system to further hone these identified stimulation patterns in patients. In addition to genetic algorithms, machine learning algorithms that require large data sets such as neural networks may be employed in the preclinical model. The preclinical model will also enable exploration in a larger parameter space due to the increased amount of testing time. This information can be used to characterize stimulation parameters and design the optimization algorithm in the clinical system.

At block 704, the machine learning or optimization algorithm may be a genetic algorithm. Stimulation parameters that describe arbitrary waveforms in the time and space domain are modulated during the optimization search. An objective function uses patient metrics to evaluate the stimulation waveform tested. The patient metrics may be objective or subjective feedback. Based on the objective function values, new stimulation parameters are selected for subsequent testing. The objective function may include several feedback components such as the pain score and a side effects score. The objective function may then be customized to fit the needs of individual patients by adjusting the objective function component weights to emphasize one aspect more than the other (e.g., pain or side effects). The genetic algorithm seeks to minimize the objective function value due to changing the stimulation parameters during the search.

In an embodiment, the genetic algorithm resides and executes on the remote control. The patient is able to decide a convenient time to use the "optimize" mode to modulate their stimulation. A stimulation waveform is selected and the patient can increase the amplitude to their comfort level. For each iteration of testing, the amount of time the stimulation is administered may be patient adjustable, for example 5 minutes. After 5 minutes, the amplitude may be decreased to 0, a new stimulation is then queued based on the patient's feedback, the amplitude is increased to the patient's comfort level, and the patient's feedback is recorded. This feedback mechanism may continue allowing the patient to optimize their stimulation. After the patient opts to finish or termination criteria is met (e.g., the objective function is satisfied), the best stimulation measured by their feedback metric may be saved and available for use. The patient may later return and optimize further using their remote control at their convenience.

Output of algorithm-derived stimulation patterns are produced at block 706. These stimulation patterns are capable of having pulse-by-pulse changes in timing such as pulse start time, pulse end time, pulse duration, and pulse interval, pulse-by-pulse changes of pulse amplitudes and pulse shape, and of having pulse-by-pulse changes in spatial location of stimulation including selection of active electrodes for each pulse, polarity and fractionalization of the modulation energy using the active electrodes. The patterns may be regular, repeating patterns, or may be non-regular in at least some of the modulation parameters (amplitude, pulse width, pulse interval, pulse polarity, and the like) in pulses groups and in groups of pulses groups.

Although some of the present disclosure discusses SCS, it is understood that other types of neuromodulation may be controlled using the systems and methods described herein. Follow is a non-exhaustive list of potential use cases.

In a neuropsychiatric use case, a number of neuropsychiatric disorders exist including major depression, obsessive compulsive disorder, addiction, anorexia, bipolar disorder, Tourette's syndrome, and the like. Brain stimulation has been investigated as a method to reduce or eliminate symptoms of such disorders.

Neuropsychiatric symptoms may be difficult to quantitatively measure, but correlations have been discovered between depression and EEG features, and between depression and autonomic features such as heart rate variability. Other autonomic measures that may be candidates include properties of respiration, galvanic skin response, or other measures related to autonomic balance. Because EEG is a candidate, it is expected that local field potential signatures also likely contain information that may be used as a feedback signal when properly processed.

As such, in embodiments, a patient with a neuropsychiatric disorder, such as depression, may receive a stimulator of a neural tissue or an endocrine tissue (e.g., brain stimulator, nerve stimulator, or spinal cord stimulator). A machine learning method may be used to optimize a pattern of stimulation, where optimization includes minimizing or maximizing a cost function of one or more objective metrics. In a related embodiment, subjective metrics, such as scores from an e-diary that a patient or caregiver records electronically into the system, may be used. Subjective measurement scores may be from standard questionnaires (e.g., the Hamilton depression rating scale) or responses to queries about general well-being or state of wellness. In yet another related embodiment, both subjective scores and objective scores may be combined and used. In yet another related embodiment, the subjective responses constitute a "ground truth" and the objective metrics may be used in conjunction with that ground truth to adapt the machine learned model. Such hybrid use of subjective and objective metrics are useful because biological systems are often not static and change over time. Such an embodiment allows the system to respond to phenomena like accommodation and habituation to the benefit of the patient.

In a cardiac function use case, it is known that stimulation of a peripheral nerve (e.g., vagus), spinal cord (e.g., SCS for angina), or DBS may affect cardiac function. Some direct and indirect measures of cardiac function are able to be measured objectively, including heart rate, heart rate variability, blood oxygen perfusion, blood pressure, patient activity, EKG properties. In embodiments, electrodes in the heart for patients with a pacemaker or defibrillator may enable sensing of atrial-ventricular coordination, cardiac EMGs, and other measures. Such measurements may serve as a candidate output target of the machine learning algorithm in addition to the neurostimulator. In some cases, these metrics may be obtained from wearable devices.

As it relates to the present disclosure, in an embodiment, a patient with a cardiac condition, such as hypertension, may receive a stimulator of a neural tissue or an endocrine tissue, and a machine learning method may be used to optimize a pattern of stimulation, where optimization includes minimizing or maximizing a cost function comprised of one or more objective metrics such as blood pressure. In a related embodiment, a preclinical model of a cardiac condition such as hypertension is configured with a stimulator of neural tissue and an optimization algorithm (such as machine learning) that has access to the quantitative metric (e.g., blood pressure) and control of a stimulation pattern and is used to optimize the stimulation pattern to achieve an ideal blood pressure. This stimulation pattern or a similar pattern may then be subsequently used as an initial setting in a patient being stimulated for the same or a related condition using a same or related stimulation target (e.g., neural tissue).

In an epilepsy use case, it is understood that epilepsy is a central nervous system disorder in which neuronal activity in the brain becomes abnormal without apparent reason, and manifests in recurring seizures or periods of unusual behavior and sensations and loss of consciousness. Seizures may be of variable duration and may vary from being nearly undetectable to significant shaking. More than 30% of patients suffer persistent seizures despite maximum antiepileptic drug therapy. There is a pressing need for alternative treatments.

Deep brain stimulation (DBS), spinal cord stimulation (SCS), vagus nerve stimulation (VNS), and peripheral nerve stimulation (PNS) are all subjects of active investigation for potential therapeutic benefit in epilepsy. In addition to their potential for treatment of patients who are refractory to treatment with drugs, these neurostimulation treatments may be used to use physiological signals of seizure to deliver therapy at opportune times, thereby reducing unnecessary stimulation and potentially improving therapy.

Patient metrics include physiological signals that are of interest in this context, such as EEG, near-infrared spectroscopy (NIRS) or other non-invasive measures of brain activity, EMG or alternate measures of muscle activity, EKG or other measures of heart activity, and clinician, patient or caregiver reports. These measurements either singly or together may be used to derive a severity metric for the pathology. For instance, spectral analysis of the scalp EEG can be used to determine seizure onset and offset, and the duration and frequency of seizures, and the latter can be used to derive an epilepsy severity metric. The metric resulting from this analysis may be used to quantify the patient's response to stimulation settings and this data is then used as input to a machine learning algorithm. The output of this algorithm includes a candidate stimulation setting that reduces disease severity.

In an overactive bladder (OAB) use case, certain nerve stimulation may be used as a treatment. OAB is a cluster of symptoms related to urinary function, the chief among which is a sudden urge to urinate. Some 30% of American men and 40% of American women suffer from overactive bladder. Behavioral interventions, medications, bladder injections, and nerve stimulation are all used as treatments of OAB. Evidence also indicates that both deep brain and spinal cord stimulation may have efficacy in treating some OAB symptoms.

OAB may be quantified by objective and subjective metrics, including void frequency, void volume, frequency of painful voids, subjective patient report of well-being and urinary urgency, etc. Effect of nerve stimulation on OAB severity may be assessed using these criteria and resulting data is fed as input to a machine learning algorithm. The output of this algorithm includes a candidate stimulation setting that may reduce symptom severity.

Other types of disorders may be treated by neuromodulation, such as movement disorders or cognitive disorders. Movement disorders include ailments like Parkinson's disease. Parkinson's disease is characterized by the cardinal symptoms of tremor, bradykinesia, and rigidity. Deep brain stimulation of the thalamus, STN (subthalamic nucleus), or GPi (Globus pallidus) is often used to improve these symptoms. However, adjustment of DBS by a neurologist is traditionally done through a serial process where the neurologist makes a program adjustment, observes a certain symptom (e.g., tremor, arm rigidity), task (e.g., finger-tapping, rapidly alternating movement), or side effect (e.g., dysarthria, muscle twitches), and then makes further adjustments. This is time-consuming and may fail to optimize the stimulation settings across all symptoms in all areas of the body.

A machine learning algorithm may be used to improve DBS programming by taking a plurality of assessments (e.g., local field potential measurements from the implanted leads, anatomical placement of the leads based on MRI and CT images, motor diary information, unified Parkinson's disease rating scale (UPDRS) scores, quantitative assessments using wearable accelerometers, speech recordings, timed motor tests), at a plurality of neurostimulation settings, and then recommending a setting based on the entirety of these data, rather than making serial adjustments after one or two observations.

Similar approaches may be used for other movement disorders such as dystonia, which is further complicated by the slow onset of DBS response and resulting difficulty of adjusting using serial observations; or essential tremor, which may show optimal tremor control for different parts of the body at slightly different stimulation settings.

Cognitive disorders include ailments such as Alzheimer's disease or Parkinson's-related dementia. DBS is also used to affect structures, such as the fornix, nucleus basalis Meynert, or entorhinal cortex. Cognitive performance is complex and may be assessed through a wide variety of methods, including working memory tasks (e.g. N-back tests, mini-cog), questionnaires and rating scales (mini-mental state examination (MMSE), Mattis Dementia Rating Scale, Alzheimer's Disease Assessment Scale-Cognition (ADAS-cog), etc.), brain imaging, mood assessments, and dual motor-cognitive tasks. Furthermore, like movement disorder evaluations, cognitive performance may be time-consuming to assess and does not lend itself to programming through serial observations. As such, a machine learning algorithm may be used to improve DBS programming by taking a plurality of assessments (e.g. local field potential measurements from the implanted leads, anatomical placement of the leads based on MRI and CT images, working memory tasks, questionnaires, rating scales, etc.) at a plurality of neurostimulation settings, and then recommending a setting based on the entirety of these data, rather than making serial adjustments after one or two observations.

Figure 8:
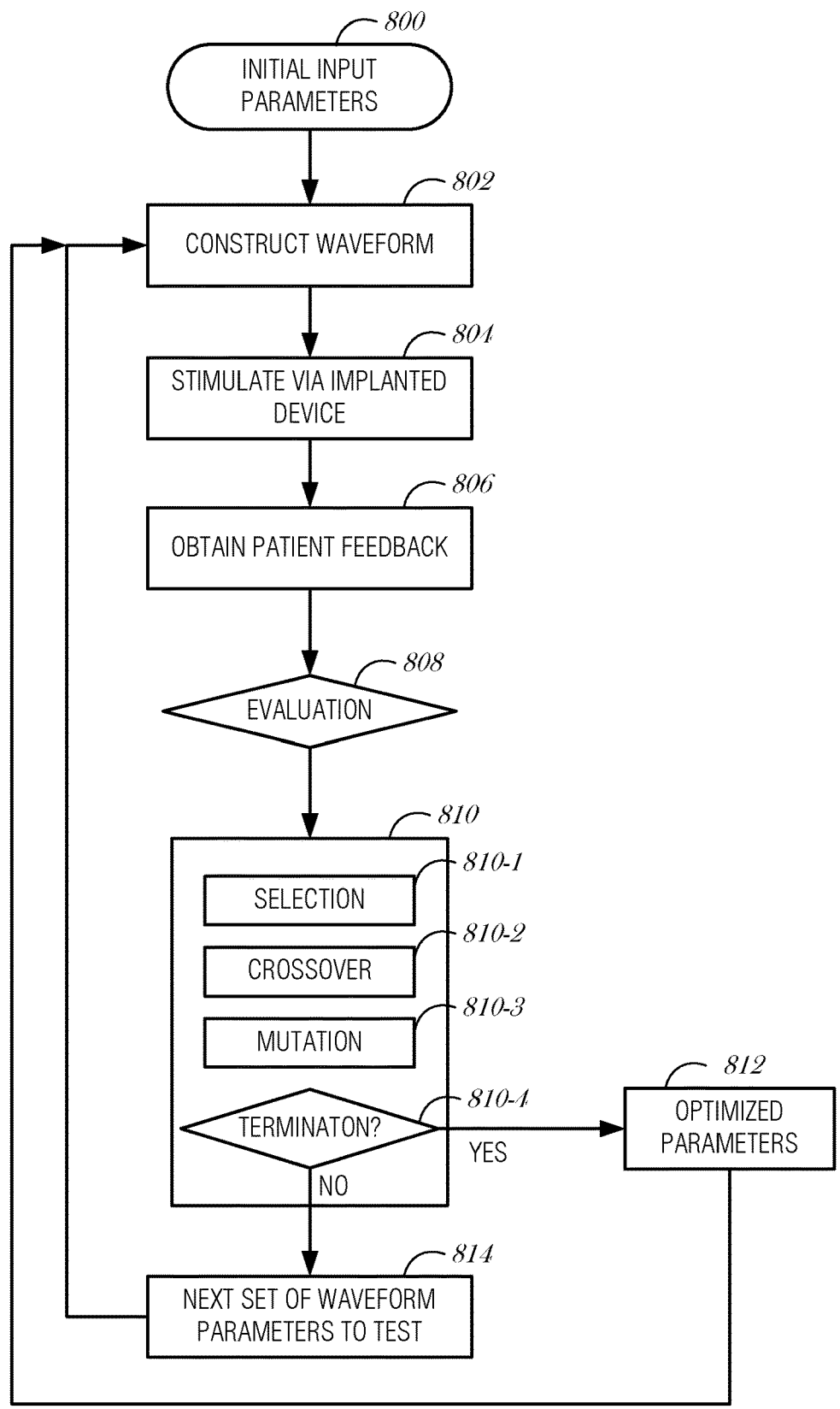
FIG. 8 illustrates, by way of example, another embodiment of data and control flow in a system that utilizes machine learning to optimize neurostimulation patterns.

FIG. 8 illustrates, by way of example, another embodiment of data and control flow in a system that utilizes machine learning to optimize neurostimulation patterns.

At stage 800, initial input parameters are accessed to construct a waveform (stage 802). Input parameters may include active contact fractionalization and waveform characteristics, such as amplitude, time delay, pulse width, or shape of each pulse in a stimulation pulse train. The constructed waveform is used to stimulate a patient via an implanted device (stage 804).

At stage 806, the patient's feedback is received. Depending on the disease or disorder being treated by the neuromodulation, the patient feedback may include various objective or subjective metrics. Objective metrics, such as the patient's EEG, medication therapy, heart rate, heart rate variability, blood oxygen perfusion, blood pressure, patient activity scores, seizure frequency or duration, seizure duration, near-infrared spectroscopy (NIRS) of brain activity, EMG or other measures of muscle activity, assessments using wearable accelerometers, timed motor tests, memory test, mood assessments, brain imaging, dual motor cognitive tasks, and the like may be used. Subjective patient feedback may include responses to questionnaires, summaries of diaries, clinician reports, or rating scales (e.g., MMSE, Mattis Dementia Rating Scale, ADAS-cog (Alzheimer's Disease Assessment Scale.—Cognition), etc.). Thus, in related embodiments, the patient feedback may be a patient metric, such as a pain score or biomarkers.

At stage 808, the patient's feedback is analyzed to determine whether additional modification to the stimulation parameters is needed. A genetic algorithm is used at stage 810 to identify one or more stimulation parameters. A genetic algorithm is a general purpose search algorithm based on the principle of evolution. The population of candidate solutions (called individuals, creatures, or phenotypes) to an optimization problem is evolved toward better solutions. Each candidate solution has a set of properties (its chromosomes or genotype) that can be mutated or altered. A genetic algorithm combines the operations of selection (stage 810-1), crossover (stage 810-2), and mutation (stage 810-3) with the goal of finding the best solution. The selection-crossover-mutation process favors better solutions from generation to generation. When the genetic algorithm reaches a termination state (e.g., a maximum number of generations) or has convergence to a solution (e.g., minimizes or maximizes an objective function) (stage 810-4), then the stimulation parameters for optimized therapy are considered to be reached (stage 812). The optimized stimulation parameters may be used until the patient's condition changes or until the parameters are no longer effective. When the genetic algorithm has not reached termination criteria or convergence state, then a next set of waveform parameters is identified and tested (stage 814). The parameters are used to construct a waveform (stage 802) and the cycle continues.

In the selection stage (810-1), chromosomes of higher fitness are selected to become the co-founders of the next generation of chromosomes. The probability of a chromosome being selected is based on a fitness function. The fitness function is used to choose which chromosomes will be elected to survive to the next generation. The fitness function is a form of an objective function used in machine learning applications. One example design of a fitness function may be to maximize pain reduction while minimizing the area affected by paresthesia. Examples of fitness selection functions include fitness proportionate selection, Bolzmann selection, tournament selection, rank selection, steady state selection, truncation selection, and local selection.

The crossover stage (810-2) is used to select two chromosomes (e.g., parents) and combine them to produce a new chromosome (e.g., offspring). Various crossover techniques may be used, such as one-point crossover, two-point crossover, or a uniform crossover. A one-point crossover function uses a single point in the parent chromosomes, and uses one parent for the first portion of the offspring chromosome and the other parent for the remainder of the offspring chromosome (after the crossover point). A two-point crossover uses two points on the chromosome to create three sections in the offspring chromosome(s), using one parent for the first and third portion of the offspring chromosome and the other parent for the second portion of the offspring chromosome. Crossover points may be chosen randomly or uniformly among chromosomes. Other functions may be used to combine chromosomes. One example function may be to equally weight each gene in the parent chromosomes and randomly select a gene from one parent chromosome for the offspring chromosome.

The mutation stage (810-3) alters one or more gene values in an offspring chromosome. The gene value may be selected randomly from a chromosome in the general gene pool. The mutated gene value may be constrained to a range (e.g., ±25% of the original gene value). Mutation prevents a selected chromosome population from becoming stagnant.

The termination of the genetic algorithm (810-4) may be achieved by executing a certain number of iterations (e.g., producing a certain number of generations), or by producing a chromosome that meets a fitness requirement. Other common terminating conditions are reaching an allocated budget (computation time/money), reaching a highest ranking solution's fitness or reaching a plateau of chromosomes such that successive iterations no longer produce better results, or combinations of these conditions.

For the purposes of this discussion, a stimulation protocol may be considered as a construction of building blocks beginning with a pulse. A pulse is single waveform and typically has a timescale in the millisecond range. A burst is a sequence of pulses and may have a timescale on the millisecond to second range. A train is a sequence of bursts and may have a timescale of millisecond, seconds, or even minutes depending on the programming used. A programming sequence is a combination of pulses, bursts, and trains. The programming sequence may also include pauses; periods with no electrical stimulation. A programming sequence may be cyclical over short durations or be non-cyclical over a short duration, but repeat over some longer "macropulse" duration.

In a pulse burst or a pulse train, the intervals between pulses may be regular or irregular. In general, the time domain includes stimulation parameters that control the timing, size, or shape of pulses. Time domain parameters include, but are not limited to, the pulse rate, pulse amplitude, pulse shape, pulse width, and interpulse delay (e.g., between bursts or trains).

In addition to the characteristics of the pulses, the location and direction of stimulation may be controlled using stimulation parameters in the space domain. Various spatial domain parameters include, but are not limited to, lead activation (e.g., which lead(s) are active/inactive), electrode activation (e.g., which electrode(s) in a lead are active/inactive) and active contact fractionalization (e.g., of the active electrodes, how much current is supplied to each active electrode in a lead).

Figure 9:
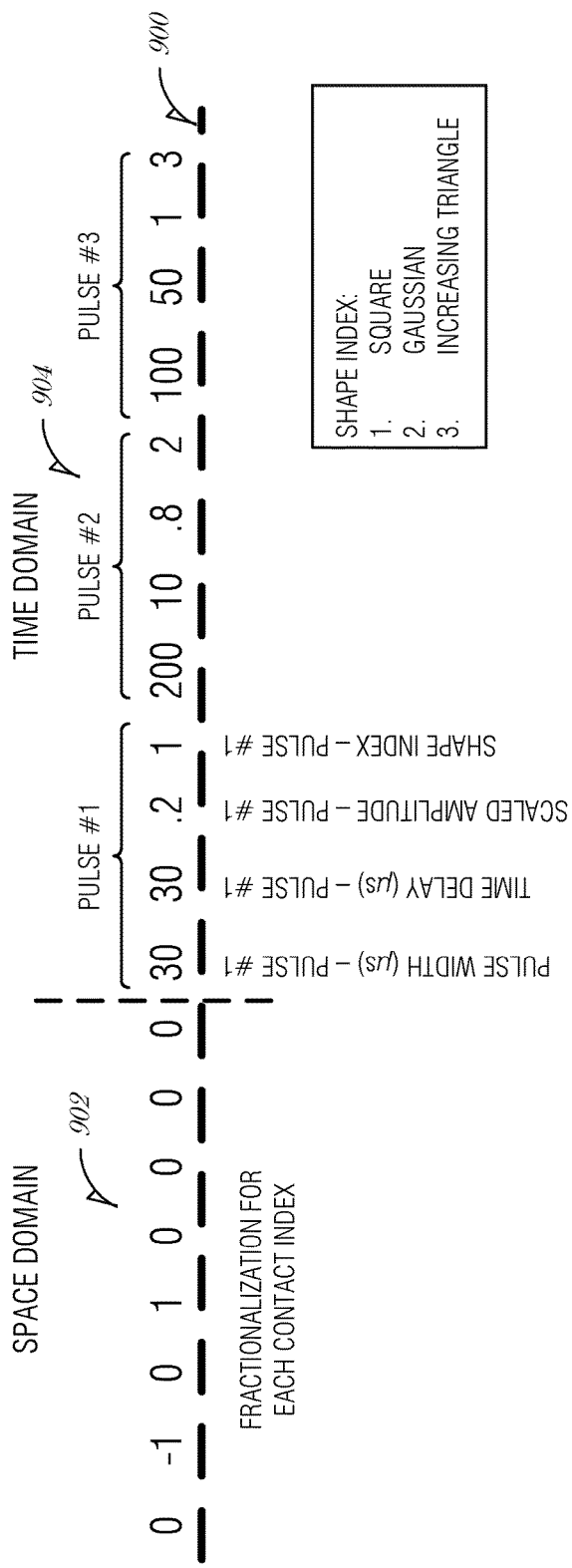
FIG. 9 illustrates, by way of example, an embodiment of constructing stimulation waveforms in space and time domains.
Figure 9:
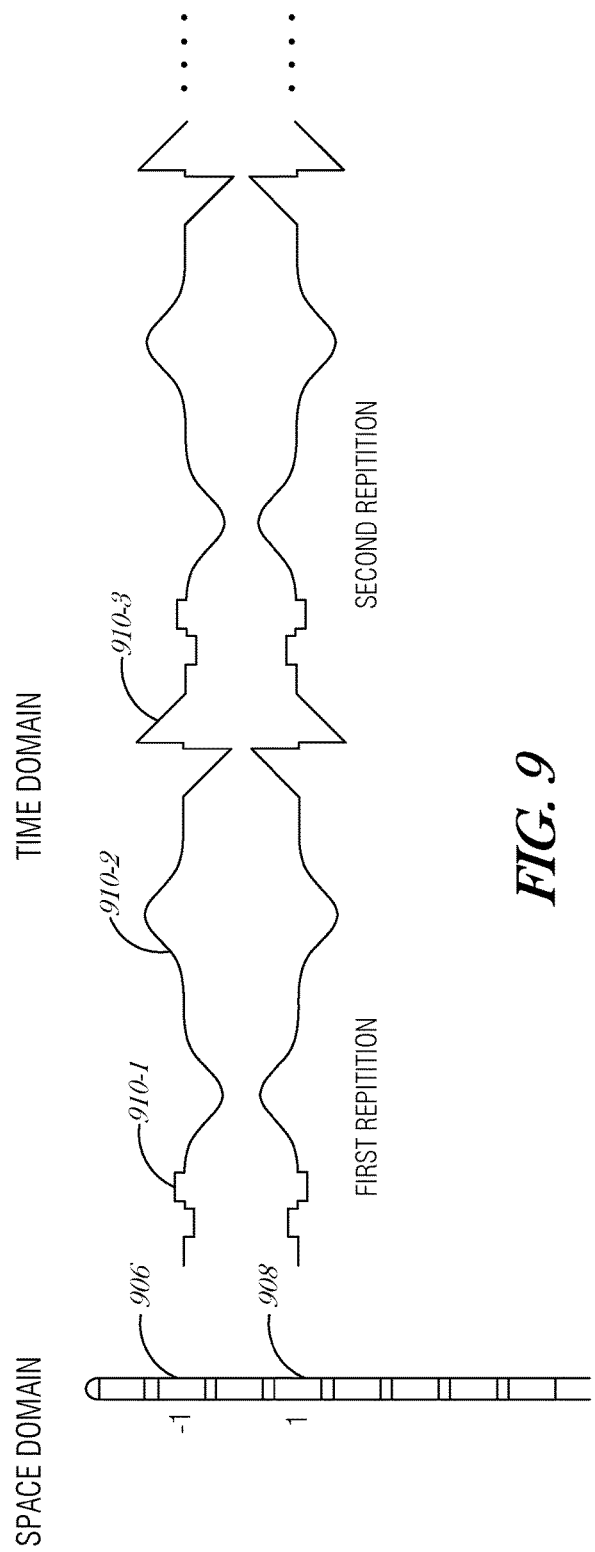

FIG. 9 illustrates, by way of example, an embodiment of constructing stimulation waveforms in space and time domains. A pulse burst may be represented as a space-time vector 900. The space-time vector 900 includes parameters for a spatial elements 902 and temporal elements 904. In this example, the space-time vector 900 parameterizes a pulse burst of three pulses. In the space domain, the spatial elements 902 include a fractionalization for each contact index is indicated. In the time domain, the temporal elements 904 include the pulse width, time delay, scaled amplitude, and shape index for each of Pulse #1, Pulse #2, and Pulse #3. The temporal element of the shape index is indicated using a "Shape Index," where for this example, a shape index of 1 indicates a square wave shape, 2 indicates a Gaussian wave shape, and 3 indicates an increasing triangle wave shape. It is understood that more or fewer wave shapes may be used.

Each element in the space-time vector 900 may be considered a gene and the space-time vector 900 may be optimized using a genetic algorithm, e.g., by selection, mutation, and crossover of the genes.

Based on the elements (parameters) in the space-time vector 900, the contact fractionalization on the second and fourth electrodes (from the distal end) 906, 908 are fractionalized with a "−1" and a "1," respectively. In the time domain, the pulses 910-1, 910-2, 910-3 are produced according the time domain parameters.

Figure 10:
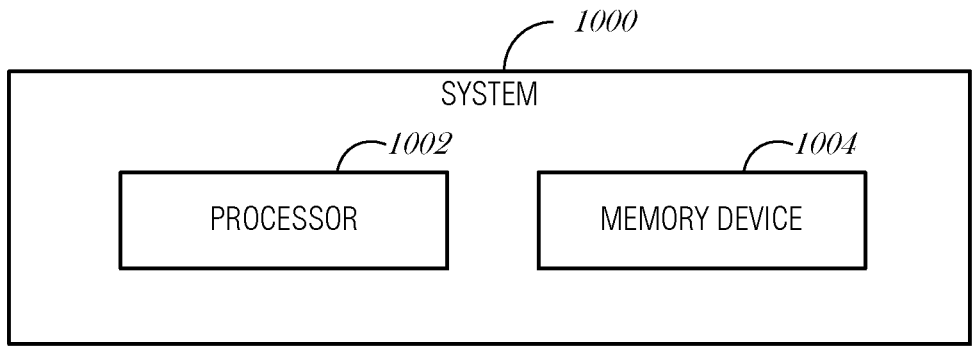
FIG. 10 illustrates, by way of example, an embodiment of a system that utilizes machine learning to optimize neurostimulation patterns.

FIG. 10 illustrates, by way of example, an embodiment of a system 1000 that utilizes machine learning to optimize neurostimulation patterns. The system 1000 may take on one of many forms. The system 1000 may be a remote control or other external device used by a patient or clinician. Alternatively, the system 1000 may be a server or cloud-based device, a network appliance, or other networked device connected via a network (or combination of networks) to a user device. The networks may include local, short-range, or long-range networks, such as Bluetooth, cellular, Wi-Fi, or other wired or wireless networks.

The system 1000 includes a processor 1002 and a memory 1004. The processor may be any single processor or group of processors that act cooperatively. The memory 1004 may be any type of memory, including volatile or non-volatile memory. The memory 1004 may include instructions, which when executed by the processor 1002, cause the processor 1002 to access a patient metric of a subject. The patient metric may be stored in memory 1004 or remote from the system 1000. For example, the patient metric may be accessed from a remote storage system using various access protocols. In an embodiment, the subject is a patient. In such an embodiment, the patient may be using the system 1000 in a clinical context. In another embodiment, the subject is an animal from a preclinical trial. The patient metric may be used to quantify a level of pain or discomfort felt by the patient and obtained via passive or active participation with the patient.

The processor 1002 may further use the patient metric as an input to a machine learning algorithm, the machine learning algorithm to search a plurality of neuromodulation parameter sets and to identify a candidate neuromodulation parameter set of the plurality of neuromodulation parameter sets, the candidate neuromodulation parameter set designed to produce a non-regular waveform that varies over a time domain and a space domain. In an embodiment, the machine learning algorithm comprises a genetic algorithm. In such an embodiment, the neuromodulation parameter set may be represented as genes in a chromosome. By using selection, crossover, and mutation, the genetic algorithm may derive an optimal neuromodulation parameter set from a pool of parameter sets. In another embodiment, the machine learning algorithm comprises a neural network.

The processor 1002 may further program a neuromodulator using the candidate neuromodulation parameter set to stimulate the subject.

In an embodiment, the system 1000 is a cloud-based system, and in such an embodiment, programming the neuromodulator includes transmitting the candidate neuromodulation parameter set to a client device of the cloud-based system. The client device may be the CP, the IPG, the ETS, or the RC in an SCS system.

In an embodiment, the patient metric is an objective pain metric. In a further embodiment, the objective pain metric is a physiological indication sensed by a sensor worn by the subject. Examples of objective pain metrics include, but are not limited to EEG activity, heart rate, heart rate variability, galvanic skin response, or the like. It is understood that other types of objective metrics may be used, such as patient activity, EEG, EKG, or EMG measurements, etc., and that the system's use of objective patient data is not limited to objective pain metrics.

In an embodiment, the patient metric is a subjective pain metric. In a further embodiment, the subjective pain metric is obtained from querying the subject. The subject may be a patient, and querying the patient may be performed via a patient device. The patient device may include a graphical user interface within which one or more prompts may be displayed to interrogate the patient about the function, performance, or efficacy of the IPG. The patient may be asked to describe the severity or location of pain, for example, using textual input, a body map, or other user interface elements to indicate subjective pain metrics. It is understood that other types of subjective metrics may be used, such as patient responses to clinicians' queries, patient diaries, questionnaires and rating scales (MMSE, Mattis Dementia Ratings Scale, ADAS-cog), etc., and that the system's use of subjective patient data is not limited to subjective pain metrics.

In an embodiment, the space domain includes at least one parameter related to fractionalization or polarity. Other aspects of the spatial domain may be included, such as those described with respect to FIG. 8.

In an embodiment, the candidate neuromodulation parameter set is designed to produce a pulse burst that varies pulse-by-pulse. Altering the amplitude, pulse shape, pulse width, or other aspects from pulse to pulse may provide additional pain management that are not available with a repeating pulse.

In an embodiment, the processor may further receive from a user, a selected parameter and focus the machine learning algorithm using the selected parameter. The selected parameter may be one or more aspects of a pulse in the time or space domain, such as amplitude.

Figure 11:
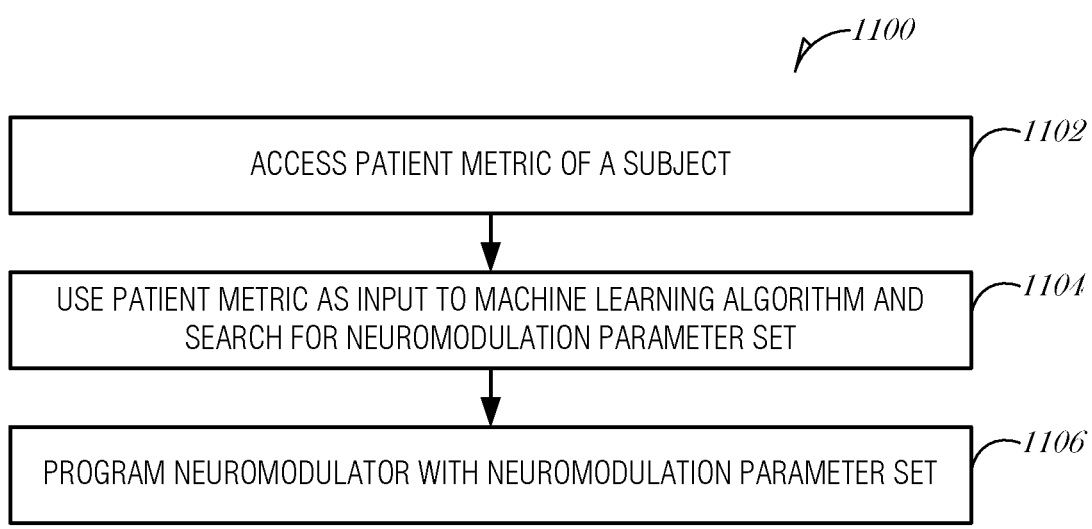
FIG. 11 illustrates, by way of example, an embodiment of a method that utilizes machine learning to optimize neurostimulation patterns.

FIG. 11 illustrates, by way of example, an embodiment of a method 1100 that utilizes machine learning to optimize neurostimulation patterns. At 1102, a patient metric of a subject is accessed at a computerized system. In an embodiment, the subject is a patient. In an embodiment, the subject is an animal from a preclinical trial.

At 1104, the patient metric is used as an input to a machine learning algorithm executing on the computerized system, the machine learning algorithm to search a plurality of neuromodulation parameter sets and to identify a candidate neuromodulation parameter set of the plurality of neuromodulation parameter sets, the candidate neuromodulation parameter set designed to produce a non-regular waveform that varies over a time domain and a space domain.

In an embodiment, the machine learning algorithm comprises a genetic algorithm. In an embodiment, the machine learning algorithm comprises a neural network.

In an embodiment, the patient metric is an objective pain metric. In a further embodiment, the objective pain metric is a physiological indication sensed by a sensor worn by the subject. In an embodiment, the patient metric is a subjective pain metric. In a further embodiment, the subjective pain metric is obtained from querying the subject.

In an embodiment, the space domain includes at least one parameter related to fractionalization or polarity.

In an embodiment, the candidate neuromodulation parameter set is designed to produce a pulse burst that varies pulse-by-pulse.

At 1106, a neuromodulator is programmed using the candidate neuromodulation parameter set to stimulate the subject. In an embodiment, the computerized system is a cloud-based system, and programming the neuromodulator comprises transmitting the candidate neuromodulation parameter set to a client device of the cloud-based system. The neuromodulator may then produce the non-regular waveform.

In an embodiment, the method 1100 further comprises receiving from a user, a selected parameter and focusing the machine learning algorithm using the selected parameter.

Figure 12:
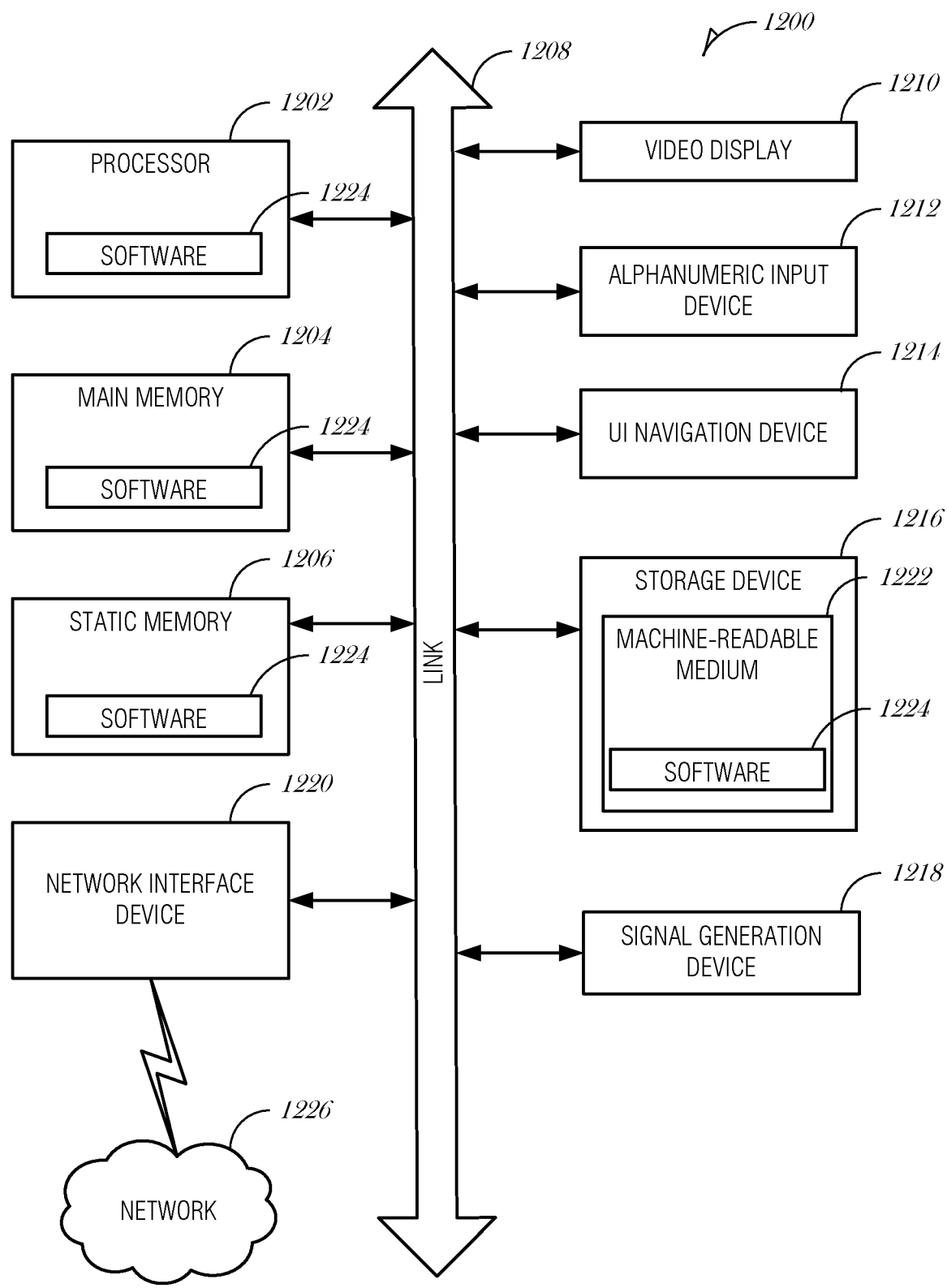
FIG. 12 is a block diagram illustrating a machine in the example form of a computer system, within which a set or sequence of instructions may be executed to cause the machine to perform any one of the methodologies discussed herein, according to an example embodiment.

FIG. 12 is a block diagram illustrating a machine in the example form of a computer system 1200, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may a personal computer (PC), a tablet PC, a hybrid tablet, a personal digital assistant (PDA), a mobile telephone, an implantable pulse generator (IPG), an external remote control (RC), a Clinician's Programmer (CP), an External Trial Stimulator (ETS), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1200 includes at least one processor 1202 (e.g., a central processing unit (CPU), a graphics processing unit (GPU) or both, processor cores, compute nodes, etc.), a main memory 1204 and a static memory 1206, which communicate with each other via a link 1208 (e.g., bus). The computer system 1200 may further include a video display unit 1210, an alphanumeric input device 1212 (e.g., a keyboard), and a user interface (UI) navigation device 1214 (e.g., a mouse). In one embodiment, the video display unit 1210, input device 1212 and UI navigation device 1214 are incorporated into a touch screen display. The computer system 1200 may additionally include a storage device 1216 (e.g., a drive unit), a signal generation device 1218 (e.g., a speaker), a network interface device 1220, and one or more sensors (not shown), such as a global positioning system (GPS) sensor, compass, accelerometer, or other sensor.

The storage device 1216 includes a machine-readable medium 1222 on which is stored one or more sets of data structures and instructions 1224 (e.g., software) embodying or utilized by any one or more of the methodologies or functions described herein. The instructions 1224 may also reside, completely or at least partially, within the main memory 1204, static memory 1206, and/or within the processor 1202 during execution thereof by the computer system 1200, with the main memory 1204, static memory 1206, and the processor 1202 also constituting machine-readable media.

While the machine-readable medium 1222 is illustrated in an example embodiment to be a single medium, the term "machine-readable medium" may include a single medium or multiple media (e.g., a centralized or distributed database, and/or associated caches and servers) that store the one or more instructions 1224. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1224 may further be transmitted or received over a communications network 1226 using a transmission medium via the network interface device 1220 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:
1. A system comprising:
a processor; and
a memory device comprising instructions, which when executed by the processor, cause the processor to:
use an assessed pain relief of a patient to identify a candidate neuromodulation parameter set for a use by a neuromodulator to deliver an electrical waveform for neuromodulation using electrodes, wherein the electrical waveform varies in distribution of modulation energy fractionalized across the electrodes; and enable the neuromodulator to treat patient pain using the candidate neuromodulation parameter set to electrically stimulate the subject using the electrical waveform that varies in the distribution.

2. The system of claim 1, further comprising a user interface configured to receive patient or clinician feedback to assess the pain relief.

3. The system of claim 1, further comprising at least one sensor configured to sense a parameter, wherein the processor is configured to use the sensed parameter to assess pain relief.

4. The system of claim 1, wherein the processor is configured to implement a machine learning algorithm to identify the candidate neuromodulation parameter set using the assessed pain relief.

5. The system of claim 1, wherein the processor is configured to use a genetic algorithm to identify the candidate neuromodulation parameter set.

6. The system of claim 1, wherein the processor is configured to use a neural network to identify the candidate neuromodulation parameter set.

7. The system of claim 1, wherein the system is a cloud-based system, and wherein the instructions to provide the candidate neuromodulation parameter set comprise instructions to transmit the candidate neuromodulation parameter set to a client device of the cloud-based system.

8. The system of claim 1, wherein the assessed pain relief is an objective metric.

9. The system of claim 1, wherein the assessed pain relief is a subjective metric.

10. The system of claim 1, wherein the processor is configured to use a machine learning algorithm, and the memory device further comprises instructions, which when executed by the processor, cause the processor to:
receive from a user, a selected parameter; and
focus the machine learning algorithm using the selected parameter.

11. The system of claim 1, wherein the electrical waveform has waveform components that vary in at least one of timing, size or shape.

12. A method comprising:
using an assessed pain relief of a subject to identify a candidate neuromodulation parameter set for a use by a neuromodulator to deliver an electrical waveform for neuromodulation using electrodes, wherein the waveform varies in distribution of modulation energy fractionalized across the electrodes;
use the candidate neuromodulation parameter set to enable the neuromodulator to electrically stimulate the subject using the electrical waveform that varies in the distribution; and
using the neuromodulator to produce the electrical waveform that varies in the distribution.

13. The method of claim 12, further comprising implementing a machine learning algorithm to identify the candidate neuromodulation parameter set using the assessed pain relief.

14. The method of claim 12, further comprising using a genetic algorithm to identify the candidate neuromodulation parameter.

15. The method of claim 12, further comprising using a neural network to identify the candidate neuromodulation parameter set.

16. The method of claim 12, further comprising:
receiving from a user, a selected parameter; and
using the selected parameter to focus an algorithm to identify a candidate neuromodulation parameter.

17. A non-transitory machine-readable medium including instructions, which when executed by a machine, cause the machine to:
use an assessed pain relief of a subject to identify a candidate neuromodulation parameter set for a use by a neuromodulator to deliver an electrical waveform for neuromodulation using electrodes, wherein the electrical waveform varies in distribution of modulation energy fractionalized across the electrodes; and
enable the neuromodulator to treat pain using the candidate neuromodulation parameter set by electrically stimulating the subject using the electrical waveform that varies in the distribution.

18. The non-transitory machine-readable medium of claim 17, wherein the instructions, which when executed by the machine, cause the machine to implement a machine learning algorithm to identify the candidate neuromodulation parameter set using the assessed pain relief.

19. The non-transitory machine-readable medium of claim 17, wherein the instructions, which when executed by the machine, cause the machine to receive patient or clinician feedback to assess the pain relief.

20. The non-transitory machine-readable medium of claim 17, wherein the instructions, which when executed by the machine, cause the machine to use at least one sensor to assess pain relief.

* * * * *